United States Patent [19]
Van Duzee et al.

[11] Patent Number: 4,504,462
[45] Date of Patent: Mar. 12, 1985

[54] PROCESS FOR MAKING A LYOPHILIZED PRODUCT FOR USE IN SKELETAL IMAGING

[75] Inventors: Barry F. Van Duzee, Westchester; Charles R. Degenhardt, Cincinnati, both of Ohio

[73] Assignee: Mallinckrodt, Inc., St. Louis, Mo.

[21] Appl. No.: 387,136

[22] Filed: Jun. 10, 1982

[51] Int. Cl.³ .................. A61K 43/00; A61K 49/00
[52] U.S. Cl. .......................... 424/1.1; 424/9; 422/61
[58] Field of Search .............. 422/61; 424/1, 1.5, 424/9

[56] References Cited

U.S. PATENT DOCUMENTS

| | | | |
|---|---|---|---|
| 4,054,645 | 10/1977 | Hill et al. | 424/1 |
| 4,104,366 | 8/1978 | Schmidt-Dunker et al. | 424/1 |
| 4,187,284 | 2/1980 | Rolleston et al. | 424/1 |
| 4,229,427 | 10/1980 | Whitehouse | 424/1 |
| 4,233,284 | 11/1980 | Fawzi | 424/1 |
| 4,247,534 | 1/1981 | Bevan | 424/1 |
| 4,313,928 | 2/1982 | Kato et al. | 424/1.5 |

FOREIGN PATENT DOCUMENTS

| | | | |
|---|---|---|---|
| 47983 | 3/1982 | European Pat. Off. | 424/1 |
| 54195 | 6/1982 | European Pat. Off. | 424/1 |
| 2618337 | 11/1976 | Fed. Rep. of Germany | 424/1 |
| 1489330 | 10/1977 | United Kingdom | 424/1 |

OTHER PUBLICATIONS

Castrovano, Journal of Nuclear Medicine, 15, 127–130, (1974).
Kahn, Experientia, 34, 1598–1600, (1978).
van den Brand, et al., Int'l. Journal of Applied Radiation and Isotopes, 30, 185–187, (1979).
Pinkerton, et al., Analytical Chemistry, 52, 1106–1110, (1980).
van den Brand, et al., Journal of Labeled Compounds and Radio-Pharmaceuticals, 18, 144–145, (1981).
Hayashi, et al., Radioisotopes, 30, 38–39, (1981).
Francis, et al., International Journal of Nuclear Medicine and Biology, 8, 145–152, (1981).
van den Brand, et al., International Journal of Applied Radiation and Isotopes, 33, 39–45, (1982).

Primary Examiner—Christine M. Nucker
Attorney, Agent, or Firm—Bernard, Rothwell & Brown

[57] ABSTRACT

A process for making a lyophilized composition, useful for skeletal imaging containing diphosphonates, stannous reductant, and an ascorbate or reductate stabilizer. The process comprises (1) preparing an aqueous solution of diphosphonate, reductant, and stabilizer, (2) adjusting the pH of the solution formed in step one to a pH in the range from about 5.5 to about 6.5, and (3) lyophilizing the pH adjusted solution.

10 Claims, No Drawings

PROCESS FOR MAKING A LYOPHILIZED PRODUCT FOR USE IN SKELETAL IMAGING

BACKGROUND OF THE INVENTION

This invention relates to radio-diagnostic agents for use in tissue imaging. More particularly, it relates to a process for preparing improved skeletal imaging products.

Scintigraphic skeletal imaging and similar radiographic techniques for visualizing other tissues are finding ever-increasing application in biological and medical research and in diagnostic procedures. Generally, scintigraphic procedures involve the preparation of radioactive agents which, upon introduction into a biological subject, become localized in specific organs, tissues, or skeletal structures that are under study. When so localized, traces, plots, or scintiphotos of the distribution of the radiographic materials can be made by various radiation detectors, e.g., traversing scanners and scintilation cameras. The distribution and corresponding relative intensity of the detected radioactive material not only indicates the position occupied by the tissue in which the radionuclide is localized, but also indicates the presence of aberrations, pathological conditions, and the like.

In general, depending on the type of radionuclide used and the organ of interest, a scintigraphic imaging agent as used in a hospital comprises a radionuclide, a carrier agent designed to target the specific organ, various auxiliary agents which affix the radionuclide to the carrier, water or other delivery vehicles suitable for injection into, or aspiration by, the patient, physiologic buffers and salts, and the like. The carrier attaches or complexes with the radionuclide, thereby localizing the material in the location where the carrier naturally concentrates in a biologic subject.

Technetium-99m ($^{99m}$Tc) is a radionuclide which is widely known for use in tissue imaging agents. This radionuclide is conveniently available commercially in the oxidized pertechnetate form ($^{99m}$TcO$_4^-$, hereinafter "pertechnetate-Tc99m"). However, the technetium in pertechnetate has a valence state of +7 and, thus, will not complex with the most commonly used carriers for radionuclide tissue imaging. This problem is easily overcome by reducing the technetium to what is believed to be the +3, +4, and/or +5 oxidation state. Thus, technetium-labeled imaging agents are generally prepared by admixing pertechnetate-Tc99m isotonic saline solution with a technetium reductant (reducing agent) such as the stannous, ferrous, or chromous salt of sulfuric or hydrochloric acid, and the desired carrier agent for targeting the organ of interest. For example, organophosphonates are known as suitable carrier agents which target technetium radionuclide to bone tissue. U.S. Pat. No. 3,983,227, Tofe and Francis, discloses the use of reducing salts with radioactive pertechnetate-Tc99m solutions and organophosphonate bone-seeking carriers to prepare skeletal imaging agents.

Technetium-containing scintigraphic imaging agents are known to be unstable in the presence of oxygen, primarily since oxidation of the reductant and/or the technetium destroys the reduced technetium/targeting carrier complex. Accordingly, such imaging agents are generally made oxygen-free by saturating the compositions with oxygen-free nitrogen gas or by preparing the agents in an oxygen-free atmosphere. Stabilization of imaging agents can also be achieved through chemical means. German Offenlegungsschrift No. 2,618,337, Tofe, published Nov. 11, 1976, discloses the use of ascorbate stabilizers with technetium imaging agents. U.S. Pat. No. 4,232,000, Fawzi, issued Nov. 4, 1980, discloses the use of gentisyl alcohol as a stabilizer for technetium imaging agents. Similarly, U.S. Pat. No. 4,233,284, Fawzi, issued Nov. 11, 1980, discloses the use of gentisic acid as a stabilizer.

Commercial products for use in skeletal imaging are generally provided in liquid or dry powder mixture "kits" with vials containing phosphate or phosphonate bone seeking carriers. Skeletal imaging agents are formed by adding pertechnetate-Tc99m, in physiological saline, to such kits. Osteoscan-HDP$^R$, which comprises the disodium salt of methanehydroxydiphosphonic acid (HMDP), stannous chloride, and gentisic acid stabilizer, is one example of a freeze-dried (lyophilized) skeletal imaging kit. Generally, such kits are produced by a process which includes the steps of:

(1) adding solid ingredients to sterile water,
(2) metering of the resulting bulk solution into individual vials,
(3) lyophilizing the solution in the vials, and
(4) packaging.

For Osteoscan-HDP$^R$, the pH of the solution, prior to lyophilization in the manufacturing process, is 3.9. It has now been discovered that adjusting the pH of the bulk solution within a certain pH range produces a freeze-dried skeletal imaging kit that, when reconstituted with pertechnetate-Tc99m solution, forms a skeletal imaging agent with improved performance. Thus, it is an object of this invention to provide an improved process for preparing imaging kits.

SUMMARY OF THE INVENTION

This invention encompasses a process for producing a dry-powder skeletal imaging kit comprising the steps of:

(1) preparing an aqueous solution of a diphosphonate, a reducing agent, and an ascorbate or reductate stabilizer;

(2) adjusting the solution formed in step 1 to a pH within the range from about 5.5 to about 6.5; and (3) lyophilizing the pH-adjusted solution.

This invention is based on the discovery that the adjustment of pH, within a particular range, during the process of manufacturing lyophilized diphosphonate-containing skeletal imaging kits yields a kit which produces a technetium skeletal imaging agent with superior imaging properties. This increased performance is manifested through faster blood clearance and higher skeletal uptake of the technetium imaging agent, i.e., the bone targeting carrier, complexed with technetium, is more quickly and more highly concentrated in bone tissue as compared to surrounding soft tissues in the body.

DESCRIPTION OF THE INVENTION

Skeletal imaging kits produced in the process of this invention comprise:

(1) a diphosphonate carrier;
(2) a stannous reductant; and
(3) an ascorbate or reductate stabilizer.

These components, as well as the process of this invention for combining the components into skeletal imaging kits, are described below.

As used herein, the term "imaging" refers to all radiographic tissue imaging processes for which the compositions made by the instant process may be used, including (but not limited to) skeletal imaging. The term "imaging agent" refers to compositions useful for tissue imaging, including (but not limited to) skeletal imaging, such compositions comprising the product of admixing pertechnetate-Tc99m, or other useful radioisotope, to an imaging kit comprising a tissue-seeking carrier, reducing agent, and stabilizer. Hence, the term "imaging kit," or "kit," refers to the imaging agent before addition of a solution of pertechnetate-Tc99m, or similar radionuclide.

Kits for use commercially preferably contain sufficient material to form multiple doses of imaging agent. Obviously, the amount of material to be incorporated in such a kit will depend upon the number of doses of imaging agent desired. Further, specific quantities of carrier, reducing agent, and stabilizer may vary according to the particular compound used. Thus, the practitioner of this invention may determine appropriate quantities by reference to literature describing particular carriers, reducing agents, and stabilizers.

COMPONENTS

Skeletal imaging carrier:

Particularly useful in the instant invention are diphosphonate imaging carriers of the formula:

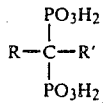

wherein R is hydrogen, alkyl containing from 1 to about 20 carbon atoms, amino alkyl, substituted aminoalkyl, alkenyl containing from 2 to about 20 carbon atoms, aryl (e.g., phenyl, naphthyl), phenylethenyl, benzyl, halogen (e.g., chlorine, bromine and fluorine), hydroxyl, amino, substituted amino (e.g., dimethylamino, diethylamino, N-hydroxy-N-ethylamino, acetylamino), -CH$_2$COOH, -CH(COOH)CH$_2$COOH, R' is hydrogen, lower alkyl (e.g., methyl, ethyl, propyl and butyl), amino, benzyl, halogen (e.g., chlorine, bromine, and fluorine), hydroxyl, or -CH$_2$COOH, and the pharmaceutically-acceptable salts thereof. Compounds of this formula are disclosed in U.S. Pat. No. 3,983,227, Tofe et al., issued Sep. 28, 1976, incorporated by reference herein. U.S. Pat. No. 4,247,534, Bevan, issued Jan. 27, 1981, incorporated by reference herein, also discloses hydroxydiphosphomethane (HMDP) as a skeletal imaging carrier and for use in agents that image myocardial infarcts.

Preferred carriers for use herein are the pharmaceutically acceptable salts of methanediphosphonic acid (MDP), methanehydroxydiphosphonic acid (HMDP), and ethane-1-hydroxy-1,1-diphosphonic acid (EHDP). Oxidronate disodium, the disodium salt of HMDP, is especially preferred. The aminodiphosphonate boneseeking carriers of the above formula are also preferred for use in the instant invention. Specifically, these aminodiphosphonate carriers are compounds and mixtures of compounds having the formulae:

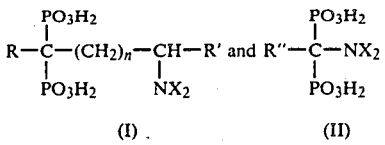

wherein n is an integer from 0 to 5; R is hydrogen, hydroxy, halogen, or amino; R' is hydrogen or alkyl containing from 1 to about 5 carbon atoms; R" is hydrogen, halogen, alkyl containing from 1 to about 8 carbon atoms, or aryl; X is hydrogen, alkyl containing from 1 to about 8 carbon atoms, aryl, alkylaryl, acetyl, or haloaryl; and the pharmaceutically-acceptable salts thereof.

Aminodiphosphonate compounds of these formulae are disclosed in the following documents incorporated by reference herein: U.S. Pat. No. 3,983,227, Tofe, issued Sept. 28, 1976; U.S. Pat. No. 4,054,598, Blum, et al., issued Oct. 18, 1977; and concurrently filed U.S. patent application Ser. No. 387,135, "Radiographic Imaging Agents," Benedict Van Duzee.

Particularly preferred aminodiphosphonate carriers include methaneaminodiphosphonic acid (AMDP), methaneaminohydroxydiphosphonic acid, methane-N-methylaminodiphosphonic acid, methane-N,N-dimethylaminodiphosphonic acid, propane-1-hydroxy-3-amino-1,1-diphosphonic acid, and ethane-1-hydroxy-2-amino-1,1-diphosphonic acid.

Reductants:

In order for these targeting agents to be useful with technetium, commercially available technetium (pertechnetate) must be reduced to from trivalent, tetravalent, and/or pentavalent technetium, which is then available to attach or complex with the targeting carrier. Reducing metal cations, such as stannous ion (Sn$^{+2}$) are known reductants for reducing the technetium in imaging compositions. The present invention incorporates one or more water-soluble, pharmaceutically-acceptable compounds which provide stannous ions when in solution, e.g., stannous chloride, stannous fluoride, stannous sulfate, and stannous citrate, herein referred to as "reductant" or "stannous reductant." Stannous chloride (SnCl$_2$) is particularly preferred.

A sufficient amount of stannous reductant must be included to ensure complete reduction of the technetium-99m added to the imaging kit. This amount, herein "effective amount," is greater than or equal to (not less than) the stoichiometric amount to reduce all of the technetium in the pertechnetate to be added to the imaging kit, i.e., when the reductant is dissolved, there must be enough stannous ion in solution to reduce technetium (+7) to a lower valence state, facilitating complexation with a diphosphonate carrier. Preferably, the effective amount of stannous tin is at least two times the molar amount of technetium to be added to the kit. The specific quantity of stannous reductant incorporated into an imaging kit encompassed by this invention may vary according to such factors as the molecular weight of the salt, the amount of pertechnetate to be added to the kit, the desired storage time of the agent made from the kit, the presence of oxidants in the agent, and the presence of anti-oxidant stabilizers, as discussed below. Preferred skeletal imaging agents, with improved performance, are formed from diphosphonate-containing kits wherein the molar ratio of diphosphonate to stannous tin in the reductant is about 65:1 or greater. As used herein "stannous tin" refers to elemental tin (Sn$^{2+}$)

contained in the reductant compound. See concurrently filed U.S. patent application Ser. No. 387,135, "Radiographic Imaging Agents," Benedict and Van Duzee (incorporated by reference herein) and concurrently filed U.S. patent application Ser. No. 387,137, "Radiographic Imaging Agents," Van Duzee (incorporated by reference herein).

Stabilizers:

The imaging kits formed in the process of this invention contain an amount, herein "stabilizing amount," of a stabilizer material sufficient to prevent or inhibit the oxidation of the reductant (e.g., oxidation of $Sn^{+2}$ to $Sn^{+4}$) during storage and/or to inhibit or reduce the reoxidation of reduced technetium-99m and/or to reduce the formation of technetium-labeled impurities which may form during use of the compositions. The stabilizers used herein are characterized by their toxicological acceptability under the conditions of use, their ability to stabilize the product for a reasonable period of storage and/or under usage conditions, and by their substantial non-interference with the delivery of the technetium radionuclide to bone mineral.

Kits made by the process of this invention include ascorbate or reductate stabilizers. "Ascorbate stabilizers" are those compounds and mixtures of compounds selected from the group consisting of ascorbic acid, erythorbic acid, substituted 5-deoxyascorbic acid, substituted 6-deoxyascorbic acid, nicotinic acid and nicotinamide complexes thereof, and the pharmaceutically-acceptable salts and esters thereof. Ascorbic acid and erythorbic acid are described in German Offenlegungsschrift No. 2,618,337, Tofe, published Nov. 11, 1976 (incorporated by reference herein). "Reductate stabilizers" are compounds and mixtures of compounds of the formula

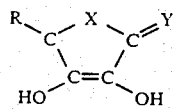

wherein X is CRR', O, or NR'; R' is hydrogen, or alkyl containing from 1 to 8 carbon atoms, Y is oxygen, sulfur, nitrogen, or $CH_2$; R is hydrogen, lower alkyl (containing from 1 to 8 carbon atoms), lower alkyl (containing from 3 to 8 carbon atoms) substituted with one or more hydroxy, halogen, amino, or thiol groups, lower alkyl (containing from 1 to 8 carbon atoms) halogen-substituted on the first and/or second carbon atom, lower alkenyl (containing from 2 to about 8 carbon atoms); nicotinic acid and nicotinamide complexes thereof; and pharmaceutically-acceptable salts, esters, and amides thereof. Reductate stabilizers of this formula are described in concurrently filed U.S. patent application, Ser. No. 387,138, "Stable Radiographic Imaging Agents," Fawzi, et al. (incorporated by reference herein).

Preferred stabilizers for use herein include ascorbic acid, sodium ascorbate, 6-bromo-6-deoxyascorbic acid, 6-chloro-6-deoxyascorbic acid, sodium-6-bromo-6-deoxyascorbate, sodium-6-chloro-6-deoxyascorbate, reductic acid, sodium reductate, 5-methylreductic acid, sodium-5-methyl reductate, and the nicotinic acid and nictotinamide complexes thereof.

As is known in the literature, stabilizer materials can chelate/complex with technetium and cause it to be deposited in uncalcified soft tissue. Since the user of the kit formed in the process of the present invention will wish to avoid all unnecessary deposition of technetium in soft tissue, it will be appreciated that the amount of stabilizer material used in the present process should not be so great as to overshadow the bone-directing effect of the diphosphonate carrier thereby interfering with the skeletal imaging. Appropriate, non-interfering amounts of stabilizer materials for use in combination with the diphosphonates may vary according to the diphosphonate and/or stabilizer used. Generally, concentrations greater than 25% of the kit composition should be avoided. For most purposes, concentrations in the range of about 0.1% to about 5% are suitable.

PROCESS

The imaging agents made with the kit produced by this process are intended for intravenous injections into humans or lower animals. Accordingly, appropriate manufacturing and operating conditions are employed so as to provide suitably sterile, pyrogen-free compositions. Although not necessary to the practice of the present invention, it is preferable to use a pharmaceutically-acceptable extender or filler to dilute the reducing and diphosphonate salts in order to simplify metering the requisite small quantities of such salts. Sodium chloride and glucose are preferred; sodium chloride is especially preferred inasmuch as its addition will assure that the resulting agent is at least isotonic even if the pertechnetate-99m solution is hypotonic (as is the case when it must be diluted with sterile water to reduce its activity.)

The preparation step in the process of this invention consists of co-dissolving the diphosphonate imaging carrier, the reducing metal salt, the stabilizer, and any optional components, in an aqueous solution. A preferred method involves dissolving the carrier and stabilizer first, and then dissolving the reducing metal salt. Preferably, sterile, deoxygenated water is used in processing and the product is stored under nitrogen. The quantity of these components incorporated into a preferred kit is enough to form multiple doses of imaging agent, as when reconstituted with a pertechnetate-Tc99m solution containing about 1 to 400 millicuries (mCi) of technetiuit-99m. (The number of doses ultimately obtained from such a kit depends upon such factors as the weight of the dosed subject and the type of tissue to be imaged.) Generally, then, a preferred kit comprises:

(a) an amount of diphosphonate carrier sufficient to target the technetium in a pertechnetate solution containing from about 1 to 400 mCi of technetium-99m;

(b) an amount of stannous chloride reducing agent sufficient to reduce the technetium in a pertechnetate solution containing from about 1 to 400 mCi technetium-99m, and (c) an amount of an ascorbate stabilizer sufficient to prevent oxidation of the reducing agent and the reduced technetium-99m.

A preferred kit formed in the process of this invention contains about 3.0 mg of the disodium salt of HMDP, about 0.24 mg stannous chloride, and about 0.84 mg ascorbic acid.

The pH of the bulk solution after the preparation step is typically below the pH encompassed by this invention. Therefore, the pH of the bulk solution is preferably adjusted through the addition of a pharmaceutically-acceptable base. Sodium hydroxide is a preferred base for this purpose. A pharmaceutically-acceptable acid, such as hydrochloric acid, may be used to adjust the pH downward, if necessary. The pH is adjusted within the range of about 5.5 to about 6.5, preferably about 6.0. This pH adjustment step may be concurrent or subsequent to the solution preparation step of this invention; i.e., a predetermined amount of base may be added during the preparation step to provide a bulk solution with the proper pH.

Lyophilization, or freeze-drying, can be done through a variety of well-known methods. The pH-adjusted diphosphonate-containing solution can be lyophilized while in bulk solution or in smaller quantities. The bulk solution is preferably placed in sterile vials fitted with a rubber septum for ease of mixing with a pertechnetate-99m solution by the user. The vials are preferably nitrogen-filled as an added protection against oxidation of the technetium reducing agent on storage. A preferred process of this invention executes the lyophilization step after the bulk solution has been metered into such mixing vials.

The compositions formed by the process of this invention are dissolved with a pertechnetate-Tc99m isotonic solution from a commercial technetium source to yield an imaging agent suitable for intravenous injection. The stability of such imaging agents is ample under ordinary hospital conditions. Administration is preferably done within about eight hours after addition of the pertechnetate-Tc99m solution. Preferably, the concentration of reagents and technetium radionuclide is sufficient that about 1 milliliter of the solution is used in an adult of about 50–100 kg body weight. One milliliter of solution is preferably injected intravenously over a period of about 30 seconds. The total dosage of radionuclide for a sharp skeletal image ranges from about 5 mCi to about 30 mCi, preferably from about 10 mCi to about 20 mCi. See also (incorporated by reference herein), U.S. Pat. No. 4,234,562, Tofe et al., issued Nov. 18, 1980; and U.S. Pat. No. 4,247,534, Bevan, issued Jan. 27, 1981.

The process of this invention is illustrated in the following non-limiting examples.

EXAMPLE 1

A kit was made, using the process of this invention, comprising the following components:

| Component | Quanity in Bulk Solution | Quantity in Kit Vial |
| --- | --- | --- |
| disodium salt of HMDP | 300 mg | 3.0 mg |
| stannous chloride | 3.2 mg | 0.032 mg |
| ascorbic acid | 81.0 mg | 0.81 mg |
| sodium chloride | 3000 mg | 30.0 mg |

The bulk solution was prepared by dissolving the HMDP, ascorbic acid, and sodium chloride in sterile, nitrogen-purged (deoxygenated) water. After dissolution of these components, the stannous chloride was added and dissolved. The resulting bulk solution had a pH of about 3.5. A sodium hydroxide solution was added so as to adjust the bulk solution to pH 6.0. Sterile, nitrogen-purged water was added to bring the volume to 100 ml.

One milliliter aliquots of the bulk solution were transferred to sterile vials which were kept under a nitrogen blanket in order to exclude oxygen. The vials were cooled and frozen under dry ice and dried under vacuum for 3 hours in a commercial lyophilization apparatus. The vials were then gradually heated to 25° C. and lyophilized for an additional 16 hours. The vials, containing the lyophilized product, were stoppered and sealed under vacuum.

An imaging agent is prepared using this kit by adding about 5 ml of a pertechnetate-Tc99m physiological saline with an activity of about 75 mCi, from a commercial technetium source. The kit is agitated until the kit components are dissolved. About 1 ml of the agent is slowly injected, over a period of about 30 seconds, into an adult human subject weighing about 75 kg. Excellent skeletal images are then obtained using a scintillation camera.

In the process described above, HMDP, MDP, EHDP, disodium MDP, and disodium EHDP are, respectively, used instead of disodium HMDP with substantially similar results. Also, in the foregoing kit, erythorbic acid, sodium ascorbate, 6-bromo-6-deoxyascorbic acid, sodium-6-bromo-6-deoxyascorbate, 6-chloro-6-deoxyascorbic acid, sodium-6-chloro-6-deoxyascorbate, reductic acid, sodium reductate, 5-methyl reductic acid, and sodium-5-methylreductate are, respectively, substituted for ascorbic acid, with substantially similar results.

EXAMPLE II

A kit is made, using the process of this invention, comprising the following components:

| Component | Quantity in Bulk Solution | Quantity in Kit Vial |
| --- | --- | --- |
| disodium salt of HMDP | 84.0 g | 3.0 mg |
| stannous chloride | 0.896 g | 0.032 mg |
| 6-bromo-6-deoxy-ascorbic acid | 19.88 g | 0.71 mg |
| sodium chloride | 1260.0 g | 45.0 mg |

A bulk solution is prepared by admixing the HMDP, 6-bromo-6-deoxyascorbic acid, and sodium chloride in sterile, deoxygenated water. Once these components are dissolved, the stannous chloride is added and dissolved. The pH of the resulting solution is determined and appropriate amount of a 1N NaOH solution added to provide a bulk solution of pH 5.5. If necessary, a 1N HCl solution is added to lower the pH to 5.5. Sterile, deoxygenated water is then added to dilute the solution to a total volume of 28 liters.

One milliliter aliquots of the bulk solution are placed in individual, sterile, deoxygenated vials. The vials are then frozen and placed under vacuum in a commercial lyophilization apparatus. Heat is applied and the product is dried for approximately 20 hours. The vials with the lyophilized product are then stoppered and sealed.

Excellent skeletal images are obtained when this kit is used to prepare an imaging agent and the agent is injected, as in Example 1. Kits are also made, using the process of this invention as described in the above Example, by adjusting the bulk solution to any pH within the range from about 5.5 to about 6.5 through the use of any pharmaceutically-acceptable base and/or acid, with substantially similar or better results. Also, in the foregoing Example, stannous fluoride, stannous sulfate, and stannous tartrate are, respectively, used instead of stannous chloride, with substantially similar results.

In the kit prepared above, methaneaminodiphosphonic acid, methane-N-methylaminodiphosphonic acid, methane-N,N-dimethylaminodiphosphonic acid, ethane-1-hydroxy-2-amino-1,1-diphosphonic acid, and the monosodium salts thereof, are substituted for disodium HMDP, with substantially similar results.

EXAMPLE III

A kit is made, using the process of this invention, comprising the following components:

| Component | Quantity in Bulk Solution | Quantity in Kit Vial |
|---|---|---|
| disodium salt of MDP | 10.00 mg | 10.0 mg |
| stannous chloride | 13.0 mg | 0.13 mg |
| ascorbic acid | 200 mg | 2.0 mg |
| glucose | 3000 mg | 30.0 mg |

Vials containing a lyophilized product are prepared as in Example 1, above. Excellent skeletal images are obtained when this kit is used to prepare an imaging agent and the agent is injected, as in Example I.

Lyophilized kits were made according to the process of this invention described in Example I, but with the pH of the bulk solution adjusted to pH 4.0, 5.0, 6.0, and 7.0. Each kit vial was then reconstituted by addition of 5 microliter of a pertechnetate-Tc99m physiological saline solution with an activity of approximately 26 mCi. A 50 microliter dose of each imaging agent thus formed was injected into a fasted rat weighing approximately 190 g.

Scintiscans were taken of rats that were injected with agents made from kits produced at each of the pH adjustments employed above. The rats were then sacrificed and blood, muscle, and bone tissue removed and placed in tared scintillation counting vials. The samples were weighed and radioassayed, along with a control sample of the original imaging agent, using a gamma-scintillation spectrometer.

The following table summarizes the distribution of the technetium-99m imaging agent in the rat body, as a function of the pH employed in the production process of the imaging kit used. This distribution is a function of the technetium-99m retention by various body tissues and is recorded below as the relative bone to muscle retention ratio and the relative bone to blood retention ratio.

TABLE

| pH | Bone/muscle | bone/blood |
|---|---|---|
| 4.0 | 570 | 20 |
| 5.0 | 518 | 121 |
| 6.0 | 593 | 160 |
| 7.0 | 571 | 138 |

This data clearly demonstrates the effect on the distribution of a technetium-99m imaging agent as a function of the pH used in the process for producing an imaging kit. This data indicates maximum bone/muscle and bone/blood retention at a kit production pH between 5.5 and 6.5. Thus, a skeletal imaging kit produced according to the process of this invention, wherein the pH of the bulk solution of components is adjusted between 5.5 and 6.5, preferably 6.0, yields an imaging agent with improved imaging qualities, i.e., increased bone/soft tissue retention and enhanced blood clearance.

What is claimed is:
1. A process, for producing a dry-powder imaging composition, comprising the steps of:
 (a) preparing a solution which comprises a diphosphonate carrier, stannous reductant, and a stabilizer in water, wherein said diphosphonate is selected from the group consisting of compounds and mixtures of compounds having the formula

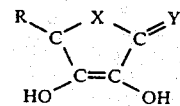

wherein $R_1$ is hydrogen, alkyl containing from 1 to about 20 carbon atoms, amino alkyl, substituted amino alkyl, alkenyl containing from 2 to about 20 carbon atoms, aryl, phenylethenyl, benzyl, halogen, hydroxyl, amino, substituted amino —CH$_2$COOH, —CH(COOH)CH$_2$COOH, $R_2$ is hydrogen lower alkyl, amino, benzyl, halogen, hydroxyl, —CH$_2$COOH, and the pharmaceutically-acceptable salts thereof, and said stabilizer is selected from the group consisting of ascorbic acid, erythorbic acid, substituted 5-deoxyascorbic acid, substituted 6-deoxyascorbic acid, pharmaceutically-acceptable salts and esters thereof, and compounds having the formula $$\begin{array}{c} R \\ \diagdown C \diagup X \diagdown C \diagup Y \\ \diagup \quad \diagdown \\ HO \quad C=C \quad OH \end{array}$$

wherein X is CRR', O, NR', R' is hydrogen, or lower alkyl, Y is oxygen, sulfur, nitrogen, or CH$_2$, R is hydrogen, lower alkyl, lower alkyl containing from 3 to 8 carbon atoms substituted with one or more hydroxy, halogen, amino or thiol groups, lower alkyl containing from 1 to 8 carbon atoms halogen-substituted on the first and/or second carbon atom, alkenyl containing from 2 to about 8 carbon atoms, nicotinic acid and nicotinamide complexes thereof; and pharmaceutically-acceptable salts, esters, and amides, and mixtures thereof;
 (b) adjusting said solution to a pH in the range from about 5.5 to about 6.5; and
 (c) lyophilizing said solution.
2. A process, for producing a dry-powder imaging composition, as recited in claim 1, wherein said diphosphonate carrier is selected from the group consisting of ethane-1-hydroxy-1,1-diphosphonic acid, methanehydroxydiphosphonic acid, methanediphosphonic acid, and the pharmaceutically-acceptable salts and mixtures thereof.
3. A process, for producing a dry-powder imaging composition, as recited in claim 1, wherein said diphosphonate carrier is selected from the group of compounds and mixture of compounds having the formulae

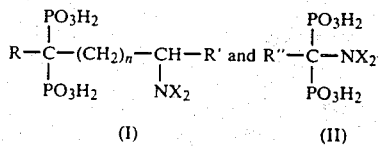

wherein n is an integer from 0 to 5; R is hydrogen, hydroxy, halogen, or amino; R' is hydrogen or alkyl containing from 1 to about 5 carbon atoms; R" is hydrogen, halogen, alkyl containing from 1 to about 8 carbon atoms, or aryl; X is hydrogen, alkyl containing from 1 to 8 carbon atoms, aryl, alkylaryl, acetyl, or haloaryl; and the pharmaceutically-acceptable salts thereof.

4. A process, for producing a dry-powder imaging composition, as recited in claim 1, wherein said stabilizer is selected from the group consisting of ascorbic acid, erythorbic acid, reductic acid, 6-bromo-6-deoxyascorbic acid, 6-chloro-6-deoxyascorbic acid, 5-methylreductic acid, nicotinic acid and nicotinamide complexes thereof, and pharmaceutically-acceptable salts and mixtures thereof.

5. A process for producing a dry powder imaging composition, as in claim 1, wherein said stannous reductant is a pharmaceutically-acceptable stannous salt.

6. A process, for producing a dry powder imaging composition, as in claim 5, wherein said stannous salt is stannous chloride.

7. A process, for producing a dry-powder imaging composition, as recited in claim 1, wherein said solution is adjusted to a pH of about 6.0.

8. A process, for producing a dry-powder imaging composition, as recited in claim 4, wherein said solution comprises: (a) about 3.0 mg of a pharmaceutically-acceptable salt of salts of methanehydroxydiphosphonic acid; (b) an effective amount, not greater than 0.15 mg, of stannous chloride; and (c) an effective amount of a pharmaceutically-acceptable salt or salts of ascorbic acid or 6-bromo-6-deoxyascorbic acid.

9. A dry-powder imaging composition comprising the product of the process recited in claim 1.

10. A dry-powder imaging composition comprising the product of the process recited in claim 8.

* * * * *